United States Patent
Shadmehri

(10) Patent No.: US 10,408,603 B2
(45) Date of Patent: Sep. 10, 2019

(54) LASER VISION INSPECTION SYSTEM AND METHOD

(71) Applicant: BOMBARDIER INC., Dorval (CA)

(72) Inventor: Farjad Shadmehri, Lachine (CA)

(73) Assignee: BOMBARDIER INC., Dorval (CA)

( * ) Notice: Subject to any disclaimer, the term of this patent is extended or adjusted under 35 U.S.C. 154(b) by 244 days.

(21) Appl. No.: 15/513,849

(22) PCT Filed: Sep. 24, 2015

(86) PCT No.: PCT/IB2015/057365
§ 371 (c)(1),
(2) Date: Mar. 23, 2017

(87) PCT Pub. No.: WO2016/046788
PCT Pub. Date: Mar. 31, 2016

(65) Prior Publication Data
US 2017/0248406 A1    Aug. 31, 2017

Related U.S. Application Data

(60) Provisional application No. 62/054,738, filed on Sep. 24, 2014.

(51) Int. Cl.
*G06K 9/00* (2006.01)
*G01B 11/00* (2006.01)
(Continued)

(52) U.S. Cl.
CPC .......... *G01B 11/002* (2013.01); *G01B 11/16* (2013.01); *G01B 11/25* (2013.01); *G01B 21/045* (2013.01);
(Continued)

(58) Field of Classification Search
CPC ....... G01B 11/002; G01B 11/16; G01B 11/25; G01B 21/045; G01B 11/02;
(Continued)

(56) References Cited

U.S. PATENT DOCUMENTS 5,562,788 A    10/1996  Kitson et al.
6,174,392 B1 *  1/2001  Reis .................. B29C 73/06
                                                156/58
(Continued)

FOREIGN PATENT DOCUMENTS

CN    102003938 A    4/2011

OTHER PUBLICATIONS

Flynn et al., "Automated fiber Placement Machine Development: Modular Heads, Tool point Programming and Volumetric Compensation Bring New Flexibility in a Scalable AFP Cell.", 14 pp.
(Continued)

*Primary Examiner* — Li Liu
(74) *Attorney, Agent, or Firm* — Norton Rose Fulbright Canada LLP

(57) ABSTRACT

There is described herein a method and system for inspecting various fabrication features of composite components, such as tow/ply location, angle deviation, and gap size, using a laser-vision assembly. In some embodiments, a tolerance for that fabrication feature is provided as an inspection feature and a laser projecting device projects the inspection feature onto the material. Alternatively or in combination thereof, a calibration feature is projected onto the material, the calibration feature comprising known dimensional information. An image acquisition device acquires an image of the material with the inspection/calibration feature(s) projected thereon. The images can be analysed automatically or manually to detect whether the fabrication features are compliant and/or to obtain measurement data of the fabrication features.

19 Claims, 15 Drawing Sheets

(51) Int. Cl.
*G01B 21/04* (2006.01)
*G01B 11/25* (2006.01)
*G01B 11/16* (2006.01)
*G01N 21/17* (2006.01)
*G01N 29/24* (2006.01)

(52) U.S. Cl.
CPC ..... *G01N 21/1717* (2013.01); *G01N 29/2418* (2013.01); *Y02B 10/30* (2013.01)

(58) Field of Classification Search
CPC ............. G01B 11/2513; G06T 7/73; G06T 2207/30108; G06T 7/0004
See application file for complete search history.

(56) References Cited

U.S. PATENT DOCUMENTS

| | | | |
|---|---|---|---|
| 6,613,169 | B2 | 9/2003 | Georgeson et al. |
| 6,799,081 | B1 | 9/2004 | Hale et al. |
| 7,039,485 | B2 | 5/2006 | Englebart et al. |
| 7,372,552 | B2 | 5/2008 | Englebart et al. |
| 7,486,805 | B2 * | 2/2009 | Krattiger ................ A61B 1/042 356/603 |
| 7,489,392 | B2 | 2/2009 | Englebart et al. |
| 7,555,404 | B2 | 6/2009 | Brennan et al. |
| 7,835,567 | B2 | 11/2010 | Oldani |
| 8,377,239 | B2 | 2/2013 | Englebart et al. |
| 8,668,793 | B2 | 3/2014 | Englebart et al. |
| 8,753,458 | B2 | 6/2014 | Englebart et al. |
| 8,770,248 | B2 | 7/2014 | Englebart et al. |
| 2005/0280803 | A1 | 12/2005 | Slesinski et al. |
| 2007/0058175 | A1 | 3/2007 | Maierhofer |
| 2009/0199948 | A1 | 8/2009 | Kisch |
| 2011/0134225 | A1 * | 6/2011 | Saint-Pierre ........... G01B 11/03 348/47 |
| 2011/0268322 | A1 * | 11/2011 | Clausen ................ G01B 11/25 382/106 |
| 2012/0099798 | A1 * | 4/2012 | Saruta ................... G01B 11/002 382/203 |
| 2012/0330453 | A1 | 12/2012 | Samak Snagari et al. |
| 2013/0033596 | A1 | 2/2013 | Crothers et al. |
| 2013/0250094 | A1 | 9/2013 | Rueb |
| 2013/0293684 | A1 | 11/2013 | Becker et al. |
| 2014/0081444 | A1 | 3/2014 | Rudberg et al. |
| 2014/0124120 | A1 | 5/2014 | Pham et al. |
| 2014/0168414 | A1 * | 6/2014 | Brumovsky ............. H04N 7/18 348/92 |
| 2017/0023490 | A1 * | 1/2017 | Ahlen ................ G01N 21/8901 |
| 2017/0261315 | A1 * | 9/2017 | Yamaguchi ............ G01C 21/28 |

OTHER PUBLICATIONS

International Search Report & Written Opinion issued in connection with PCT Application No. PCT/IB2015/057365 dated Dec. 11, 2015.

1st Office Action dated Jan. 4, 2019 in connection with Chinese patent application No. 201580051117.5.

\* cited by examiner

α = 1.3278°
0.5" x cos (α) = 0.49986 → Pixel in X = 0.49986/302 + 0.00165"

α = 0.7563°
0.5" x cos (α) = 0.49995 → Pixel in Y = 0.49995/306 + 0.00165"

LASER VISION INSPECTION SYSTEM AND METHOD

CROSS-REFERENCE TO RELATED APPLICATIONS

This application claims priority under 35 U.S.C. 119(e) to U.S. application No. 62/054,738 filed Sep. 24, 2014, entitled "Laser Vision Inspection System and Method", the entire contents of which are hereby incorporated by reference.

TECHNICAL FIELD

The present invention relates to the field of machine vision inspection and more particularly, to the projection of features onto a part for inspecting various manufacturing features.

BACKGROUND OF THE ART

Composite components (or materials) are generally made from two or more constituent materials with significantly different physical or chemical properties. When combined, they produce a component with characteristics different from the individual materials, with the aim of using the benefit of both.

When manufacturing composite components using a manufacturing process such as Automated Fiber Placement (AFP) or Automated Tape Layering (ATL), inspecting the dimensional requirements of the manufactured components is an important part of the manufacturing process.

Known methods for performing dimensional inspection involve gathering data via manual inspection using a hand-held laser tracker, and having an operator compare the measured data with theoretical data from a Computer-Aided Design (CAD) file. In the case of a composite component having many plies, manual inspection of the fibers of each ply of the component is extremely time consuming. Another shortcoming of manual inspection is that it is dependent on the hand and eye skills of the operator, which makes it harder to validate the inspection at a later time.

There is therefore a need to improve the inspection phase of the manufacturing process for certain components.

SUMMARY

There is described herein a method and system for inspecting various fabrication features of composite components, such as tow/ply location, angle deviation, and gap size, using a laser-vision assembly. In some embodiments, a tolerance for that fabrication feature is provided as an inspection feature and a laser projecting device projects the inspection feature onto the material. Alternatively or in combination thereof, a calibration feature is projected onto the material, the calibration feature comprising known dimensional information. An image acquisition device acquires an image of the material with the inspection/calibration feature(s) projected thereon. The images can be analysed automatically or manually to detect whether the fabrication features are compliant and/or to obtain measurement data of the fabrication features.

In accordance with a first broad aspect, there is provided a method for inspecting a composite component. The method comprises positioning the composite component in a three-dimensional coordinate system; causing a laser-generated inspection feature to be projected onto the composite component at a location in the three-dimensional coordinate system corresponding to a fabrication feature of the composite component, the inspection feature having geometric parameters associated with a dimensional tolerance for the fabrication feature; acquiring an image of the composite component with the inspection feature projected thereon and visible in the image; and determining compliance of the fabrication feature based on a relative position of the fabrication feature with respect to the inspection feature.

In some embodiments, determining compliance of the fabrication feature comprises a visual inspection of the fabrication feature relative to the laser-generated inspection feature. In some embodiments, the method further comprises outputting a non-compliant signal for non-compliant fabrication features. In some embodiments, the method further comprises converting the dimensional tolerance into the inspection feature.

In some embodiments, the inspection feature is a three-dimensional inspection feature adapted to a shape of the composite component. In some embodiments, the inspection feature is a tolerance window having a width W corresponding to the dimensional tolerance. In some embodiments, the inspection feature is a reference point and a reference line having a length L and positioned with respect to the reference point in accordance with the dimensional tolerance.

In some embodiments, the fabrication feature is one of a tow location, a gap size, and a fiber angle deviation.

In some embodiments, the laser-generated inspection feature is projected onto the composite component at a predetermined incident angle with respect to a normal to a surface of the composite component.

In some embodiments, the method is performed as the composite component is manufactured, for each ply of the composite component.

In some embodiments, a plurality of inspection features are projected onto the composite component for inspection of a plurality of fabrication features. In some embodiments, the plurality of inspection features comprise at least two different inspection features for projecting onto at least two different fabrication features.

In some embodiments, the method further comprises replacing the projected inspection feature in the acquired image by a virtual inspection feature.

In some embodiments, the method further comprises acquiring another image of the composite component without the inspection feature projected thereon and adding a virtual inspection feature on the other image to represent the projected inspection feature, and wherein determining compliance of the fabrication feature comprises determining compliance using the other image.

In accordance with another broad aspect, there is provided a system for inspecting a composite component on a manufacturing tool. The system comprises at least one laser projecting device configured for projecting an inspection feature onto the composite component at a location corresponding to a fabrication feature of the composite component, the inspection feature having geometric parameters associated with a dimensional tolerance for the fabrication feature; and at least one image acquisition device positioned with respect to the composite component and the laser projecting device to acquire an image of the composite component with the inspection feature projected thereon and visible in the image.

In some embodiments, the system further comprises a controller operatively connected to at least one of the at least one laser projecting device and the at least one image acquisition device, and configured for controlling at least one of projection of the inspection features and acquisition of images.

In some embodiments, the system further comprises a controller connected to at least one of the at least one laser projecting device and the at least one image acquisition device, and configured for comparing the fabrication feature and the inspection feature to determine compliance of the fabrication feature with the dimensional tolerance. In some embodiments, the controller is further configured for controlling at least one of projection of the inspection features and acquisition of images.

In some embodiments, the controller is further configured for converting the dimensional tolerance into the inspection feature. In some embodiments, the at least one laser projecting device is fixed. In some embodiments, the at least one image acquisition device is displaceable along a rail or frame. In some embodiments, the at least one image acquisition device has at least one of panning, tilting and zooming capabilities. In some embodiments, the at least one image acquisition device is a video camera.

In some embodiments, the at least one laser projecting device is positioned to project at a predetermined incident angle with respect to a normal to a surface of the composite component.

In some embodiments, the inspection feature is a three-dimensional inspection feature adapted to a shape of the composite component. In some embodiments, the inspection feature is a tolerance window having a width W corresponding to the dimensional tolerance. In some embodiments, the inspection feature is a reference point and a reference line having a length L and positioned with respect to the reference point in accordance with the dimensional tolerance.

In some embodiments, the fabrication feature is one of a tow location, a gap size, and a fiber angle deviation.

In some embodiments, the laser projecting device is further configured for scanning targets on the manufacturing tool to determine a location of the composite component in a three-dimensional space.

In accordance with another broad aspect, there is provided a computer readable medium having stored thereon program code for inspecting a composite component. The program code is executable by a processor for positioning the composite component in a three-dimensional coordinate system; causing a laser-generated inspection feature to be projected onto the composite component at a location in the three-dimensional coordinate system corresponding to a fabrication feature of the composite component, the inspection feature having geometric parameters associated with a dimensional tolerance for the fabrication feature; acquiring an image of the composite component with the inspection feature projected thereon and visible in the image; and determining compliance of the fabrication feature based on a relative position of the fabrication feature with respect to the inspection feature.

In accordance with yet another broad aspect, there is provided a method for inspecting a composite component. The method comprises positioning the composite component in a three-dimensional coordinate system; causing a laser-generated calibration feature to be projected onto the composite component at a location in the three-dimensional coordinate system corresponding to a fabrication feature of the composite component, the calibration feature having known dimensional information; acquiring an image of the composite component with the calibration feature projected thereon and visible in the image; determining calibration data for calibrating the image from the calibration feature and the known dimensional information in the image as acquired; and determining a measurement of the fabrication feature using the calibration data and a relative position of the fabrication feature with respect to the calibration feature.

In some embodiments, determining calibration data from the calibration feature comprises converting a pixel size to a dimensional value. In some embodiments, determining calibration data from the calibration feature comprises transforming a point in an image coordinate system into a local coordinate system on the composite component. In some embodiments, determining calibration data from the calibration feature comprises transforming a point in the local coordinate system to a global coordinate system in a virtual model of the composite component. In some embodiments, determining calibration data comprises determining an angle of a line drawn between two points on the calibration feature in the image coordinate system. In some embodiments, determining calibration data comprises determining a distance between two points on the calibration feature in the image coordinate system.

In some embodiments, determining a measurement of the fabrication feature comprises determining a tow location on the composite component. In some embodiments, determining a measurement of the fabrication feature comprises measuring an angle of a fiber of the composite component. In some embodiments, determining a measurement of the fabrication feature comprises measuring a gap size on the composite component.

In some embodiments, the method further comprises determining compliance of the fabrication feature by comparing the measurement of the fabrication feature to a predetermined tolerance. In some embodiments, the predetermined tolerance is embedded in the calibration feature as a geometric parameter thereof.

In some embodiments, determining a measurement of the fabrication feature comprises receiving a selection of at least one point in the image from a graphical user interface. In some embodiments, determining a measurement of the fabrication feature comprises outputting the measurement of the fabrication feature on a graphical user interface.

In some embodiments, the method further comprises converting the known dimensional information into the calibration feature.

In some embodiments, the calibration feature is a grid having a known origin and known distances between nodes. In some embodiments, the calibration feature is a pair of crosses relatively positioned to have an angle of a line drawn between corresponding intersection points correspond to a predetermined angle. In some embodiments, the calibration feature is a double cross having a spacing between two parallel lines correspond to a predetermined distance.

In some embodiments, the laser-generated calibration feature is projected onto the composite component at a predetermined incident angle with respect to a normal to a surface of the composite component.

In some embodiments, the method is performed as the composite component is manufactured, for each ply of the composite component. In some embodiments, plurality of calibration features are projected onto the composite component for inspection of a plurality of fabrication features. In some embodiments, the plurality of calibration features comprise at least two different calibration features for projecting onto at least two different fabrication features.

In some embodiments, the method further comprises replacing the projected calibration feature in the acquired image by a virtual calibration feature.

In some embodiments, the method further comprises acquiring another image of the composite component without the calibration feature projected thereon, and wherein determining a measurement of the fabrication feature comprises determining the measurement using the other image.

In some embodiments, the method further comprises acquiring another image of the composite component without the calibration feature projected thereon, and adding a virtual calibration feature on the other image to represent the projected calibration feature.

In accordance with another broad aspect, there is provided a system for inspecting a composite component on a manufacturing tool. The system comprises at least one laser projecting device configured for projecting a calibration feature onto the composite component at a location corresponding to a fabrication feature of the composite component, the calibration feature having known dimensional information; and at least one image acquisition device positioned with respect to the composite component and the laser projecting device to acquire an image of the composite component with the calibration feature projected thereon and visible in the image.

In some embodiments, the system further comprises a controller operatively connected to at least one of the at least one laser projecting device and the at least one image acquisition device, and configured for controlling at least one of projection of the calibration feature and acquisition of images.

In some embodiments, the system further comprises a controller connected to at least one of the at least one laser projecting device and the at least one image acquisition device, and configured for determining calibration data for calibrating the image from the calibration feature and the known dimensional information in the image as acquired; and determining a measurement of the fabrication feature using the calibration data and a relative position of the fabrication feature with respect to the calibration feature.

In some embodiments, the controller is further configured for controlling at least one of projection of the calibration feature and acquisition of images.

In some embodiments, the at least one laser projecting device is fixed. In some embodiments, the at least one image acquisition device is displaceable along a rail or frame. In some embodiments, the at least one image acquisition device has at least one of panning, tilting and zooming capabilities. In some embodiments, the at least one image acquisition device is a video camera.

In some embodiments, the at least one laser projecting device is positioned to project at a predetermined incident angle with respect to a normal to a surface of the composite component.

In some embodiments, the laser projecting device is further configured for scanning targets on the manufacturing tool to determine a location of the composite component in a three-dimensional space.

In some embodiments, determining calibration data from the calibration feature comprises converting a pixel size to a dimensional value. In some embodiments, determining calibration data from the calibration feature comprises transforming a point in an image coordinate system into a local coordinate system on the composite component. In some embodiments, determining calibration data from the calibration feature comprises transforming a point in the local coordinate system to a global coordinate system in a virtual model of the composite component. In some embodiments, determining calibration data comprises determining an angle of a line drawn between two points on the calibration feature in the image coordinate system. In some embodiments, determining calibration data comprises determining a distance between two points on the calibration feature in the image coordinate system.

In some embodiments, determining a measurement of the fabrication feature comprises determining a tow location on the composite component. In some embodiments, determining a measurement of the fabrication feature comprises measuring an angle of a fiber of the composite component. In some embodiments, determining a measurement of the fabrication feature comprises measuring a gap size on the composite component.

In some embodiments, the controller is further configured for determining compliance of the fabrication feature by comparing the measurement of the fabrication feature to a predetermined tolerance. In some embodiments, the predetermined tolerance is embedded in the calibration feature as a geometric parameter thereof.

In some embodiments, determining a measurement of the fabrication feature comprises receiving a selection of at least one point in the image from a graphical user interface. In some embodiments, determining a measurement of the fabrication feature comprises outputting the measurement of the fabrication feature on a graphical user interface.

In some embodiments, the controller is further configured for converting the known dimensional information into the calibration feature.

In some embodiments, the calibration feature is a grid having a known origin and known distances between nodes. In some embodiments, the calibration feature is a pair of crosses relatively positioned to have an angle of a line drawn between corresponding intersection points correspond to a predetermined angle. In some embodiments, the calibration feature is a double cross having a spacing between two parallel lines correspond to a predetermined distance.

In some embodiments, the controller is further configured for causing the at least one image acquisition device to acquire another image of the composite component without the calibration feature projected thereon, and adding a virtual calibration feature on the other image to represent the projected calibration feature.

In some embodiments, the controller is further configured for causing the at least one image acquisition device to acquire another image of the composite component without the calibration feature projected thereon, and wherein determining a measurement of the fabrication feature comprises determining the measurement using the other image.

In some embodiments, the controller is further configured for replacing the projected calibration feature in the acquired image by a virtual calibration feature.

In accordance with yet another broad aspect, there is provided a computer readable medium having stored thereon program code for inspecting a composite component. The program code is executable by a processor for positioning the composite component in a three-dimensional coordinate system; causing a laser-generated calibration feature to be projected onto the composite component at a location in the three-dimensional coordinate system corresponding to a fabrication feature of the composite component, the calibration feature having known dimensional information; acquiring an image of the composite component with the calibration feature projected thereon and visible in the image; determining calibration data for calibrating the image from the calibration feature and the known dimensional information in the image as acquired; and determining a measurement of the fabrication feature using the calibration data and a relative position of the fabrication feature with respect to the calibration feature.

Further details of these and other aspects of the subject matter of this application will be apparent from the detailed description and drawings included below.

BRIEF DESCRIPTION OF THE DRAWINGS

The appended drawings are as follows:

FIG. 9b is an exemplary embodiment of a calibration step using the calibration feature of FIG. 9a;

FIG. 9c is an exemplary embodiment of a measurement step using the calibration feature of FIG. 9a;

It will be noted that throughout the appended drawings, like features are identified by like reference numerals.

DETAILED DESCRIPTION

A method for inspecting a composite component manufactured using an automated manufacturing process will be described. For illustrative purposes, the process described is an Automated Fiber Placement (AFP) process but other automated manufacturing processes, such as Automated Tape Layering (ATL), may be used. In order to manufacture a composite component using AFP, fiber strips (tows) are laid along a mold in multiple layers in order to create a composite component having the shape of the mold. The fiber strips are placed along the mold in accordance with fiber laying trajectories that are input into the AFP machine to create a given component in accordance with a set of design parameters.

The composite component may comprise various materials, such as but not limited to cements, concrete, reinforced plastics, metal composites, polymeric composites and ceramic composites. For example, the composite component may be composed of composite fiber-reinforced plastics. The composite component may be used for various applications, including but not limited to buildings, bridges, spacecrafts, aircrafts, watercrafts, land vehicles including railway vehicles, and structures such as wind turbine blades, swimming pool panels, bathtubs, storage tanks, and counter tops.

The inspection method is used to assess various fabrication features of the composite component. Examples of fabrication features are ply/tow location, angle deviation, and gap size. These features result from the fabrication process and have specific permissible limits of variation. The permissible limits of variation, referred to herein as dimensional tolerances, may be with respect to a size, a position, an angle, a spacing and any other measurable value or physical property of the composite component. Dimensional tolerances are used to ensure that the composite component meets the geometric and stress requirements for the part and/or for the assembly of the part with other components. Proper compliance with dimensional tolerances will ensure that the composite component as manufactured has the desired form, fit, performance and functions as intended.

A dimensional tolerance may be visually represented on the composite component using a laser projecting device. The laser projecting device projects an inspection feature having specific geometric parameters associated with the dimensional tolerance for the fabrication feature onto the composite component in the region of the fabrication feature. The inspection feature may be a shape, a point, a set of points, or any combination thereof. Alternatively or in combination therewith, the laser projecting device projects a calibration feature having known dimensional information onto the composite component.

Figure 1A:
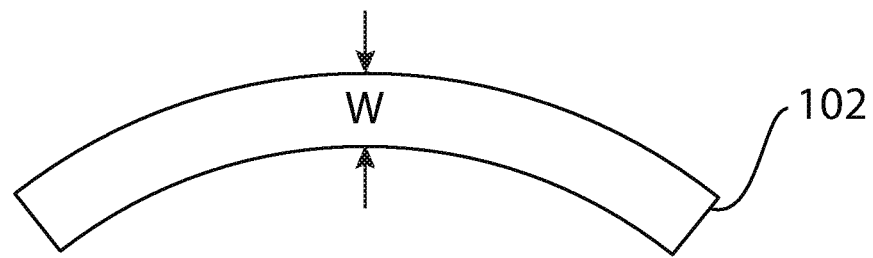
FIG. 1a illustrates an exemplary tolerance window as an inspection feature for tow location.

FIG. 1a illustrates an exemplary inspection feature for tow location. The inspection feature comprises a tolerance window 102 having a width W. In this example, the dimensional tolerance for placement of the end of the tow is ±q units. The width W is thus set to 2*q units. The tolerance window 102 may be shaped to match the shape of the composite component, which may be flat, have single curvature (surface that curves in one direction) or have double curvature (surface that curves in two directions). In this example, the composite component is dome-shaped and the tolerance window is thus curved in accordance with the dome-shape.

Figure 1B:
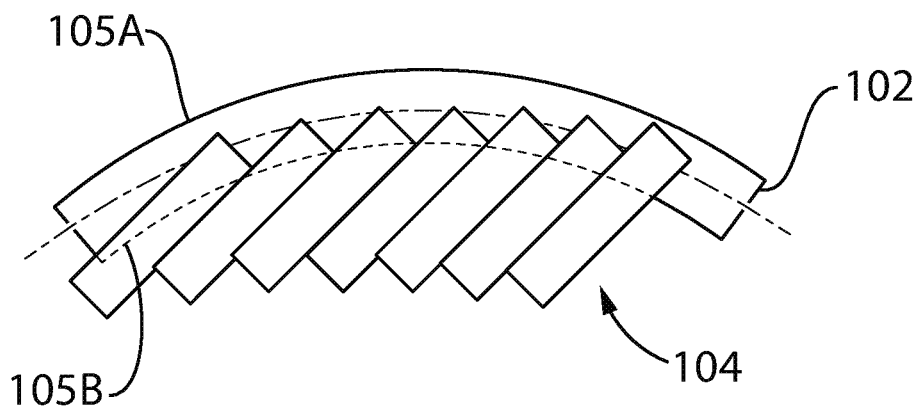
FIG. 1b illustrates the tolerance window of FIG. 1a projected onto a composite component that is compliant.
Figure 1C:
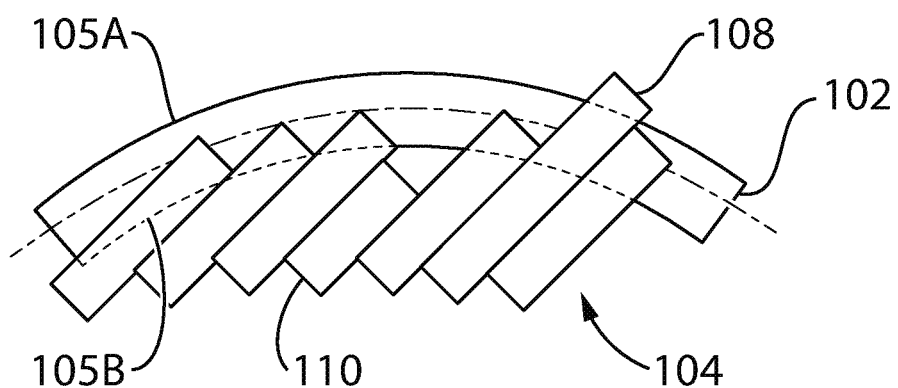
FIG. 1c illustrates the tolerance window of FIG. 1a projected onto a composite component that is non-compliant.

FIG. 1b illustrates the tolerance window 102 projected onto a set of tows 104 placed on a mold. The tolerance window 102 is positioned in space such that its center is at a nominal position for the location of the tows 104 and its upper edge 105a is at +q units from the nominal position while its lower edge 105b is at −q units from the nominal position. As shown, the ends of all tows 104 fall within the tolerance window 102 and thus tow location is compliant with the specified dimensional tolerances. FIG. 1c illustrates an example where a first tow 108 exceeds the upper edge 105a of the tolerance window 102 and a second tow 110 exceeds the lower edge 105b of the tolerance window 102. These tows 108, 110 are thus not compliant with the specified dimensional tolerances. Note that other configurations may be considered compliant, depending on the settings associated with the tolerance window 102. For example, tow location may be considered compliant if the left-most corner of a tow or a right-most corner of a tow fall within the tolerance window 102. Other variants will be understood by those skilled in the art.

Figure 1D:
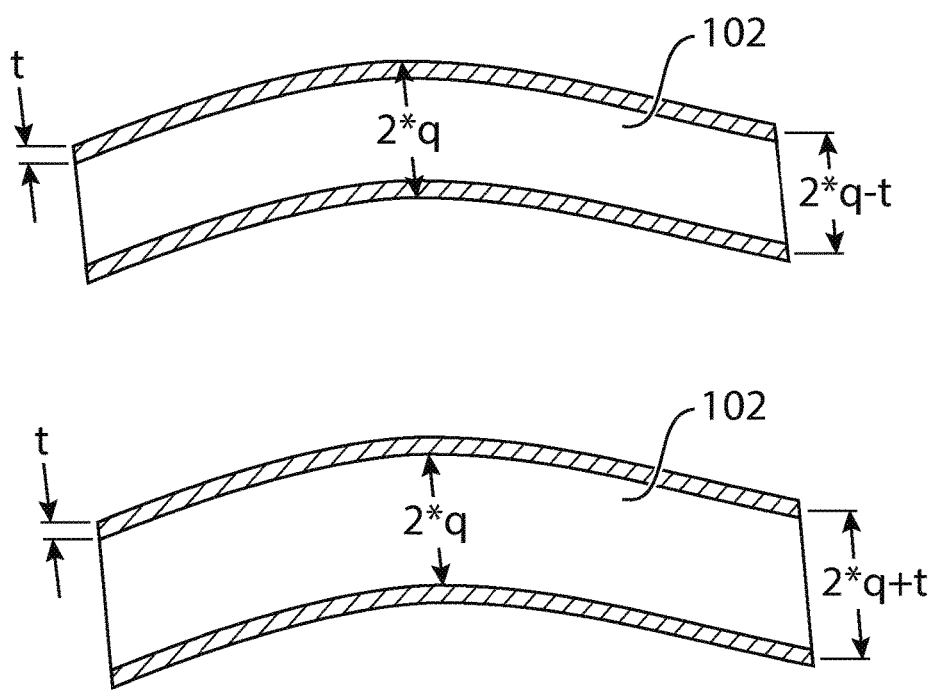
FIG. 1d illustrates exemplary tolerance windows with compensation for a laser thickness t.

In some embodiments, the width W of the tolerance window 102 is adjusted to compensate for the thickness of the laser line. This is illustrated in FIG. 1d, wherein W is set to 2*q+t or 2*q−t and t is the thickness of laser line.

Figure 2A:
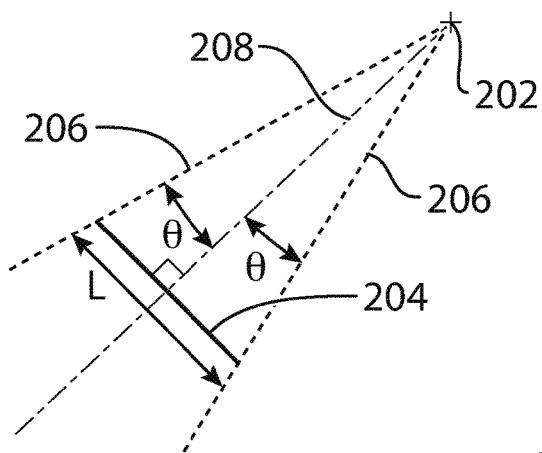
FIG. 2a illustrates an exemplary reference point and reference line as an inspection feature for fiber angle.
Figure 2B:
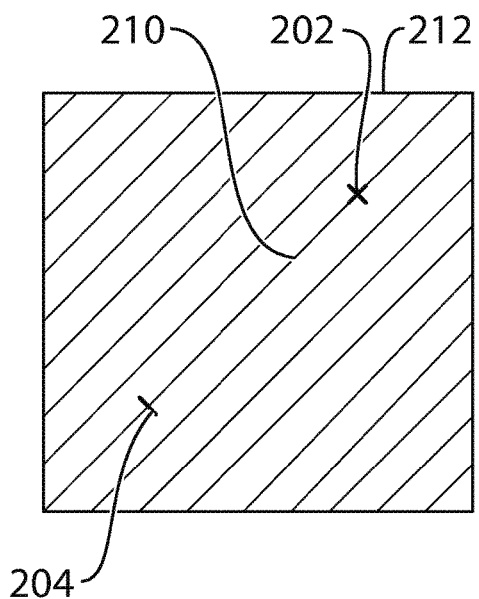
FIG. 2b illustrates the reference point and reference line of FIG. 2a projected onto a composite component that is compliant.
Figure 2C:
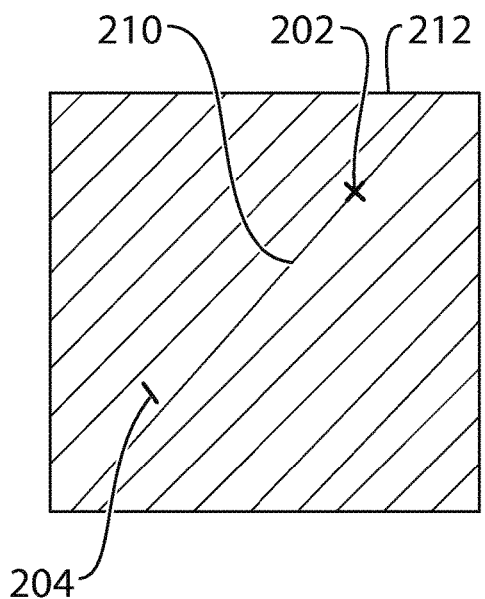
FIG. 2c illustrates the reference point and reference line of FIG. 2a projected onto a composite component that is non-compliant.
Figure 2D:
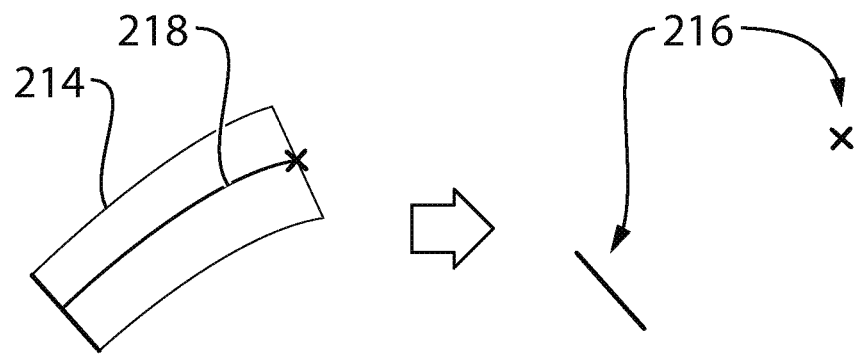
FIG. 2d illustrates an example of inspection features extracted from a shape along a curved path.
Figure 2E:
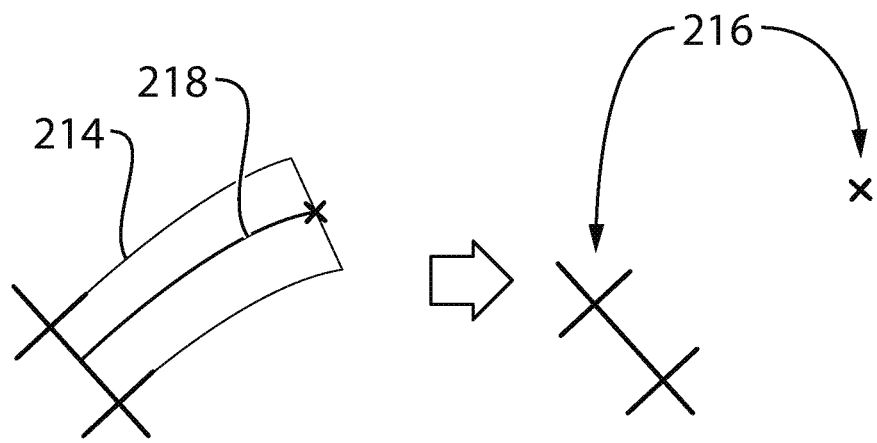
FIG. 2e illustrates another example of inspection features extracted from a shape along a curved path.

FIG. 2a illustrates an exemplary inspection feature for angle deviation. A reference point 202 and a reference line 204 are provided to represent visually a dimensional tolerance of ±θ°. The reference line 204 has a length L. An angle θ is formed between a first line 206, which extends between the reference point 202 and an end of the reference line 204, and a second line 208, which is perpendicular to the reference line 204 and crosses the reference point 202. FIG. 2b illustrates an example where the reference point 202 and reference line 204 are projected onto a composite component 212. Fiber 210 is shown to be compliant with the dimensional tolerances for this fabrication feature as it crosses both the reference point 202 and the reference line 204. In FIG. 2c, the fiber 210 is shown to be non-compliant as it does not cross reference line 204 and thus its angle deviation exceeds θ°. In order to locate the reference point at the right location (aligning the reference point with the fabrication feature), offsetting the reference point may be required. In some embodiments, angle deviation may be verified along a curved path. FIGS. 2d and 2e illustrate how angle deviation may be translated to profile tolerance by extracting the inspection features 216 from a curved shape 214 using a curved line 218.

Figure 3A:
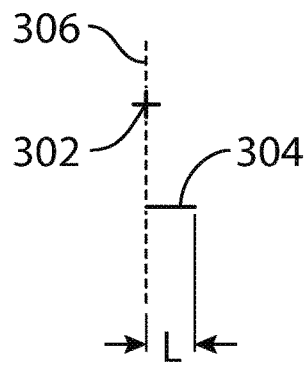
FIG. 3a illustrates an exemplary reference point and reference line as an inspection feature for gap size.
Figure 3B:
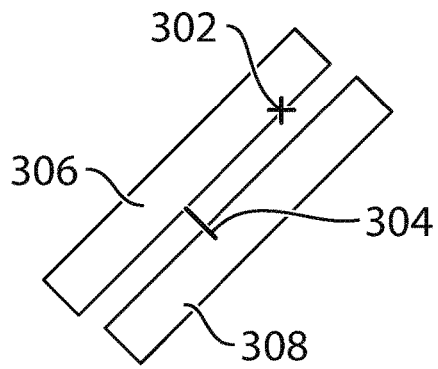
FIG. 3b illustrates the reference point and reference line of FIG. 3a projected onto a composite component that is compliant.
Figure 3C:
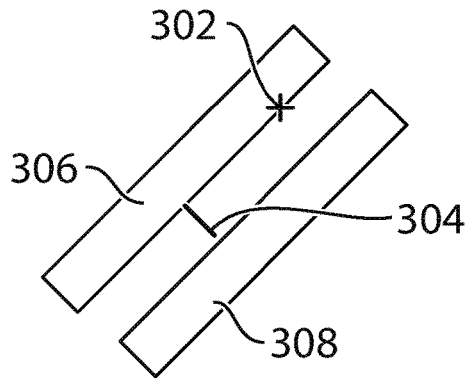
FIG. 3c illustrates the reference point and reference line of FIG. 3a projected onto a composite component that is non-compliant.
Figure 3D:
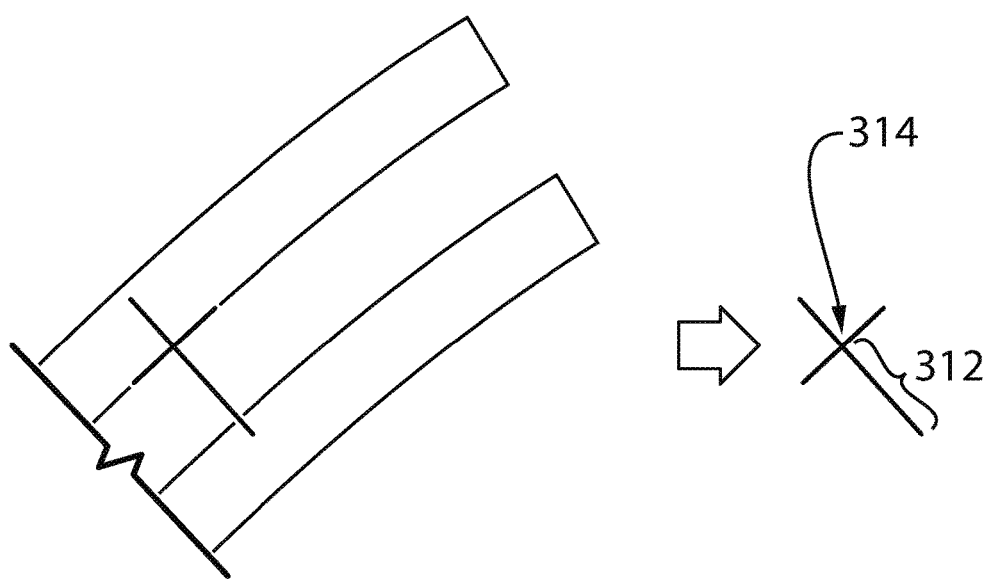
FIG. 3d illustrates an example of an inspection feature as two intersecting lines for gap size.

FIG. 3a illustrates an exemplary inspection feature for gap size. A reference point 302 and a reference line 304 are provided to represent visually a dimensional tolerance of S units for a gap between adjacent tows. The reference line 304 has a length L set to S units. One end of the reference line 304 is aligned with the reference point 302. FIG. 3b illustrates an example where the reference point 302 and the reference line 304 are projected onto a composite component and positioned with respect to a first tow 306 that is separated from an adjacent tow 308 by a gap. The gap size is shown to be compliant with the dimensional tolerances for this fabrication feature as it is smaller than the length of the reference line 304. In FIG. 3c, the gap size between tow 306 and tow 308 is shown to be non-compliant as it exceeds the length L of the reference line 304.

The embodiments shown in FIGS. 1 to 3 are examples of inspection features and they may be varied or modified. For example, the dimensional tolerances for tow location may be represented visually using a line having a length L that is positioned in a 3D coordinate system, instead of a tolerance window. Similarly, the dimensional tolerances for gap size may be represented visually by a tolerance window having a width W corresponding to the maximum allowable gap size between two adjacent tows. A pair of lines that cross and have predetermined lengths may also be used to assess gaps, as is illustrated in FIG. 3d, using at a reference point 314 and gage 312. Other variants will be understood by those skilled in the art.

Figure 4:
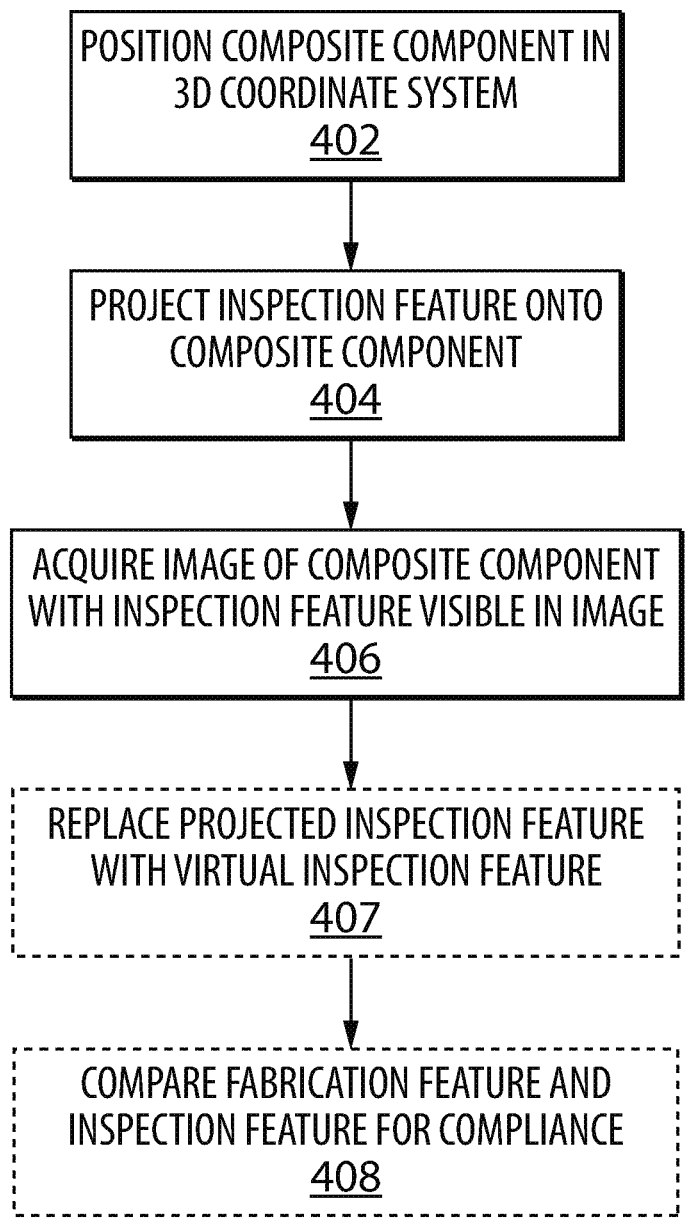
FIG. 4 is a flowchart of an exemplary method for inspecting a composite component.

Turning now to FIG. 4, there is illustrated a flowchart of an exemplary method for inspecting a composite component. A first step 402 of positioning the composite component in a three-dimensional coordinate system is provided. The composite component may be formed on a tool such as a mold or mandrel. The tool may have a known and fixed position in the coordinate system and simply laying fibers in an automated manner to form each ply of the component may constitute positioning the component in the coordinate system. In some embodiments, targets are provided on the tool and scanned in order to establish its position in the coordinate system. In other embodiments, a reference point having a known and fixed position, other than the tool itself, is used to determine the position in space of the composite component. Other techniques to position the component in a frame of reference will be readily understood. Any frame of reference may be used to represent the position and orientation in space of the composite component.

Once positioned in space, the inspection features are projected onto the composite component 404 using the three-dimensional coordinate system established in step 402. The inspection features may therefore be accurately positioned on the composite component 404 in relation to respective fabrication features. As described above, the inspection features are laser-generated and may comprise shape(s), line(s), point(s), or any combination thereof. The inspection feature is provided with geometric parameters that are associated with the dimensional tolerance of the fabrication feature under inspection. As per step 406, an image of the composite component having the inspection feature projected thereon is acquired. This may be done by displacing an image acquisition device to an appropriate position to acquire the image. The inspection feature is projected on the composite component so as to be visible in the acquired image. In some embodiments, the method comprises a step of converting the dimensional tolerances into the inspection features prior to projection onto the composite component. Note that an image may comprise more than one fabrication feature with a corresponding inspection feature projected thereon. The simultaneously projected inspection features may be for a same or a different type of fabrication feature. All of the inspection features for a same or different type of fabrication feature may be projected together or sequentially for any given ply. One or more images may be acquired for all of the inspection features for any given ply.

In some embodiments, the method for inspecting composite components comprises replacing the projected inspection feature in the acquired image with a virtual inspection feature, as per 407. Two images may be acquired; a first image with a projected inspection feature and second image without a projected inspection feature. Image processing software may be used to identify the projected inspection feature in the first image and insert the virtual inspection feature in its place in the second image. Alternatively, the virtual inspection feature may simply be overlaid or superimposed on the projected inspection feature. The virtual inspection feature may provide better visibility and compensate blur spots and/or discontinued laser lines from the laser projection.

In some embodiments, the acquired image is archived for analysis and/or verification at a later time. Alternatively, the method may comprise a step 408 of comparing the fabrication feature and the inspection feature to determine compliance of the fabrication feature with the dimensional tolerance. Compliance is thus determined based on a relative position of the fabrication feature with respect to the laser-generated inspection feature. In some embodiments, the comparison may be performed manually by an operator viewing the acquired image on a display screen. In such cases, determining compliance is performed by the operator who visually inspects the positioning of the fabrication feature relative to the laser-generated inspection feature. As described above in relation to FIGS. 1B and 1C, the operator's visual inspection may simply involve determining whether all or part of the fabrication feature falls within and/or intersects/aligns with the tolerance range defined by the projected inspection feature. That is to say, no specialized equipment is used and an operator can quickly assess compliance of the fabrication feature visually, without any need for measurement of the exact positioning of the tows.

Alternatively, determining compliance of the fabrication feature may be automated using image processing tools. In some embodiments, the automated comparison comprises determining whether the fabrication feature lies within the projected feature, and/or intersects/aligns with the projected inspection feature. A fabrication feature (or at least a portion of a fabrication feature) that lies within the projected inspection feature and/or intersects/aligns with the projected inspection feature may be determined to be a compliant fabrication feature, and a fabrication feature (or at least a portion of a fabrication feature) that lies at least partially outside the projected inspection feature and/or does not intersect/align with the projected inspection feature may be determined to be non-compliant. The comparison may further comprise outputting a non-compliant signal for non-compliant fabrication features. The signal may be sent to a technician advising of the need for repair. In such a case, the signal may comprise information regarding the non-compliant fabrication feature, such as its location and the non-compliant parameters. The signal may also be used to accept or reject composite components, as a function of a total number of non-compliant fabrication features, the nature of the non-compliant fabrication features, and/or the degree of severity of the non-compliance. Other factors may also be used to accept or reject the composite component once non-compliant fabrication features have been detected.

In some embodiments, the comparison is performed in real-time as the component is manufactured. For example, fibers are placed on a mold to form a first ply, one or more inspection features are projected onto the first ply, images are acquired, and the fabrication features of the first ply are assessed. If all fabrication features meet their respective dimensional tolerances, fibers are placed on the mold to form a second ply on top of the first ply. One or more fabrication features are projected onto the second ply, images are acquired, and the fabrication features of the second ply are assessed. This procedure may be repeated for all of the plies of the composite component and/or for multiple composite components. Non-compliant fabrication features may be repaired in real-time and the inspection features may be projected onto a ply having repaired fabrication features to validate the repairs. New images may be acquired and once the repaired fabrication features are found to be compliant, the procedure continues for a subsequent ply and/or a subsequent component.

Figure 5:
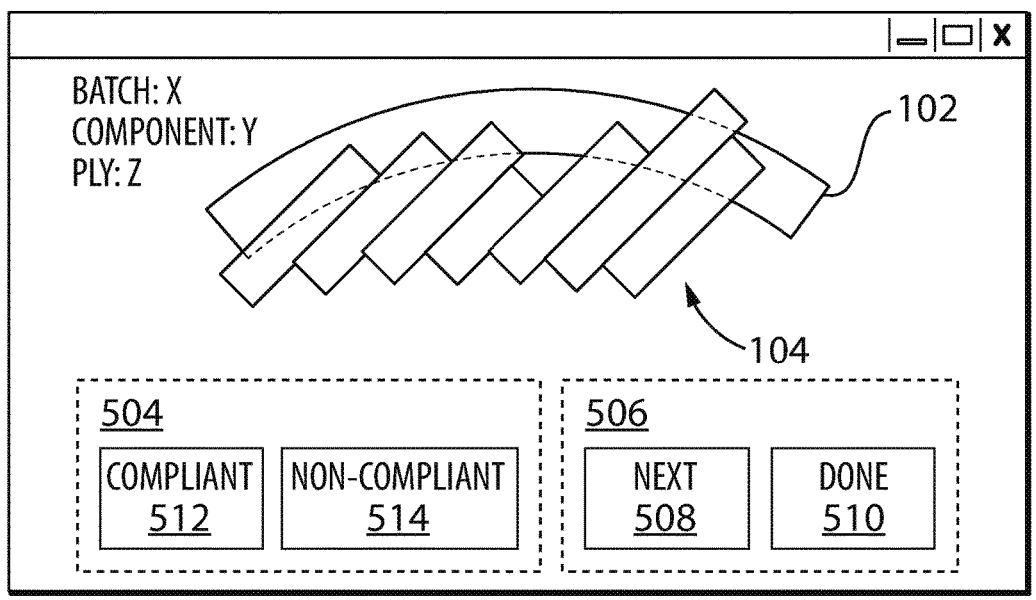
FIG. 5 is an exemplary graphical user interface for comparing a fabrication feature with an inspection feature.

FIG. 5 is an exemplary graphical user interface (GUI) 502 for performing manual assessment of the fabrication features. The tolerance window 102 and the tows 104 are displayed on the GUI 502 for visual assessment of whether the tow locations match the geometric parameters of the inspection feature. An actionable object 504 is provided. The actionable object 504 is any graphical control element that invokes an action when activated by a user. It is selectable by a user for submitting a verdict of "compliant" 512 or "non-compliant" 514 for the displayed fabrication feature. In some embodiments, other information related to the non-compliant features may be entered into the GUI if the "non-compliant" 514 option is selected. Some examples of such information are the number of out of tolerance tows and the location of out of tolerance tows. The actionable object 504 may take various forms, such as a button, a slider, an icon, a list box, a spinner, a drop-down list, a link, a tab, a scroll bar, and/or any combination thereof. In this example, another actionable object 506 is also provided with two elements, a "next" button 508 to have a new fabrication feature displayed on the GUI 502 and a "done" button 510 to confirm that inspection is complete or that all fabrication features of a ply/component/batch have been inspected. Note that a "previous" button (not shown) may also be provided to enable an operator to go back to already inspected features. More or less elements may be used for the actionable objects 504, 506. For example, vision system functions may control functions related to image acquisition, including but not limited to, manual intervention (to allow the user to override the preset settings and take control of the image acquisition device by joystick, or other user control device) and pre-set zoom-in (to provide a more in depth view of the fabrication feature). Laser system functions may control functions related to laser projection, including but not limited to, laser auto calibration (to automatically scan the targets for positioning the component in 3D space) and offsetting (used for alignment of the reference points). Other additional information may be provided in the GUI 502. For example, the dimensional tolerances for a given fabrication feature may be provided in legend format next to the image. Identification data for the ply and/or component and/or batch under inspection may also be provided.

Figure 6:
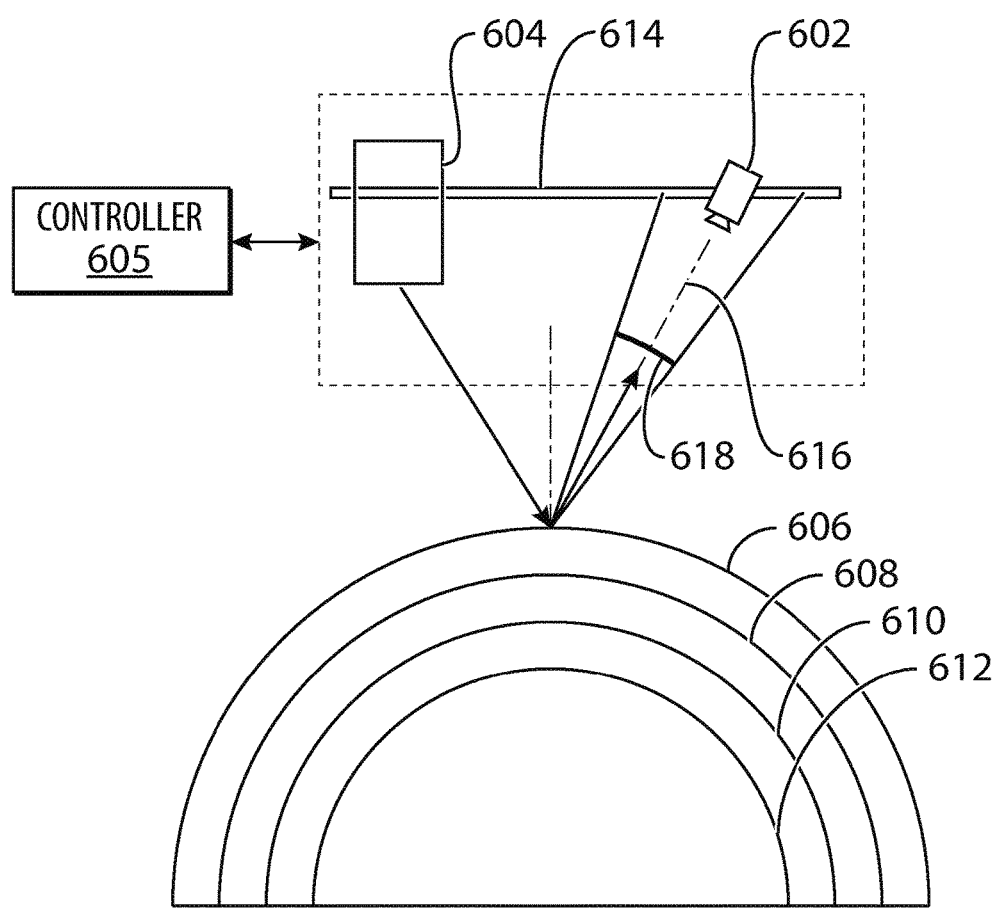
FIG. 6 is an exemplary set-up for a system for inspecting a composite component.

Turning now to FIG. 6, there is shown schematically a set-up for projecting the laser-generated inspection features and acquiring images thereof. In this example, an image acquisition device 602 and a laser projecting device 604 are provided. The image acquisition device 602 may be any instrument capable of recording images that can be stored directly, transmitted to another location, or both. These images may be still photographs or moving images such as videos or movies. In some embodiments, the image acquisition device 602 is a video camera having 1080 horizontal lines of vertical resolution and Full Frame high-definition image transmission capabilities. In some embodiments, the image acquisition device 602 and/or the laser projecting device 604 are mounted on a rail/frame system 614 so as to be displaced automatically or manually to a desired position. The image acquisition device 602 may have pan-tilt-zoom control features and 36× optical zoom with 12× digital zoom. The laser projecting device 604 may be any instrument capable of projecting visible changing laser beams on a surface. It may consist of lasers, mirrors, galvanometers and other optical components housed in an enclosure. It may contain one laser light source for single color projection or multiple laser light sources for multiple color projection. The laser projecting device 604 may be composed of laser diodes, Diode-Pumped Solid State (DPSS) lasers, or gas lasers. In some embodiments, the laser projecting device 604 has an accuracy of ±0.006 inches/5 feet, a beam width of 0.02 inch Full width at half maximum (FWHM), and a dimension of 12×4.5×4.5 inches. In other embodiments, the laser projecting device 604 has an accuracy of ±0.010 inches.

The image acquisition device 602 and laser projecting device 604 may be positioned using various configurations. The appropriate configuration may depend on the material on which the laser-generated inspection features are projected and/or the thickness of each layer of the composite component and the total number of layers. For example, a cured material may have a diffuse surface and thus light is reflected at all angles substantially equally. An uncured material may have a specular surface and incoming light will be reflected into a single outgoing direction. Therefore, for cured materials, the image acquisition device 602 may be positioned more freely and still be capable of capturing an image such that the inspection features are visible thereon. In the case of uncured materials, the image acquisition device 602 may be positioned to capture the single light ray reflected from the surface of the composite component. With regards to material thickness, if the surface of the material is specular and reflects only in a single direction, the position of the reflected ray may change as the thickness of the composite component increases. The laser projection device 604 may be positioned to project at a limited incident angle (such as ±30°) with respect to the normal to the surface of the composite component in order to limit the error arising from the variations due to thickness of the material.

In FIG. 6, the composite component is shown to have four plies 606, 608, 610, 612. The laser projecting device 604 is positioned to project substantially at a limited angle to the normal vector of the surface of the uppermost ply 606 while the image acquisition device 602 is positioned to capture the reflected ray 616. In some embodiments, the image acquisition device 602 is provided with a cone having viewing angle 618 around the reflected ray 616 where as long as the image acquisition device 602 is located inside this cone, it can acquire a visible image of a feature. It also allows for some error in positioning. For example, the viewing angle 618 may be 20°, 30°, or any other acceptable viewing angle.

In some embodiments, the laser projecting device 604 is fixed and the image acquisition device 602 is displaceable using, for example, a rail system or a frame system. Alternatively, the image acquisition device 602 may be fixed and the laser projecting device 604 may be displaceable. Also alternatively, both the laser projecting device 604 and the image acquisition device 602 are displaceable. In some embodiments, a plurality of image acquisition devices 602 are provided at various positions and a selection is made as a function of a position of the fabrication feature on the composite component. Similarly, a plurality of laser projecting devices 604 may also be provided at various positions and a selection is made as a function of a position of the fabrication feature on the composite component.

A controller 605 may be provided to control displacement of the image acquisition device 602 and/or the laser projecting device 604 and/or to select an appropriate one for imaging and projecting, respectively. The controller 605 may control the tool rotation angle to position it in an appropriate angle for inspection. The controller 605 may also be provided to manage image acquisition and projection of the inspection features. The controller 605 may communicate with the laser projecting device 604 and/or image acquisition device 602 using various means. For example, wire-based technology, such as electrical wires or cables, and/or optical fibers may be used. Wireless technologies, such as RF, infrared, Wi-Fi, Bluetooth, and others may also be used.

In some embodiments, the setup of FIG. 6 may also be used to obtain inspection data, such as ply location, angle deviation, and gap sizes. Such inspection data may be obtained directly from images acquired by the image acquisition device 602. However, as the image acquisition device 602 may have zoom/pan/tilt capabilities, it may be challenging to calibrate. For this purpose, calibration features may be projected onto the composite component using the laser projecting device 604 for calibrating the acquired images. Calibration features may be, similarly to the inspection features, a shape, a point, a set of points, or any combination thereof. For example, a calibration feature may be a grid, a cross, or a circle. In some embodiments, same features may be used for both inspection and calibration. Such features may thus comprise calibration information and inspection information. Calibration information corresponds to known data from the feature, such as known distances between node points of a grid, or a known diameter of a circle. Inspection information corresponds to dimensional tolerance information for a given fabrication feature.

The calibration features may be used to transform a point in the image (in pixel coordinates) to a local curvilinear coordinate system ($P_1$, $P_2$) on a surface of the component to a global coordinate system (X, Y, Z) in a theoretical CAD model. A Z coordinate may be based on the measured (X, Y) coordinates from the theoretical CAD model. A calibrated image may thus be output with coordinate information (X, Y, Z) for each point. Note that projected calibration features may also be replaced or superposed with virtual calibration features. In some embodiments, two images are acquired using the image acquisition device 602, one with the calibration features projected thereon and one without the calibration features projected thereon. During the calibration process, virtual calibration features can be added to the image without the projected calibration features. In addition, once calibration is done, the image without the projected features may be used to obtain inspection data.

Figure 7:
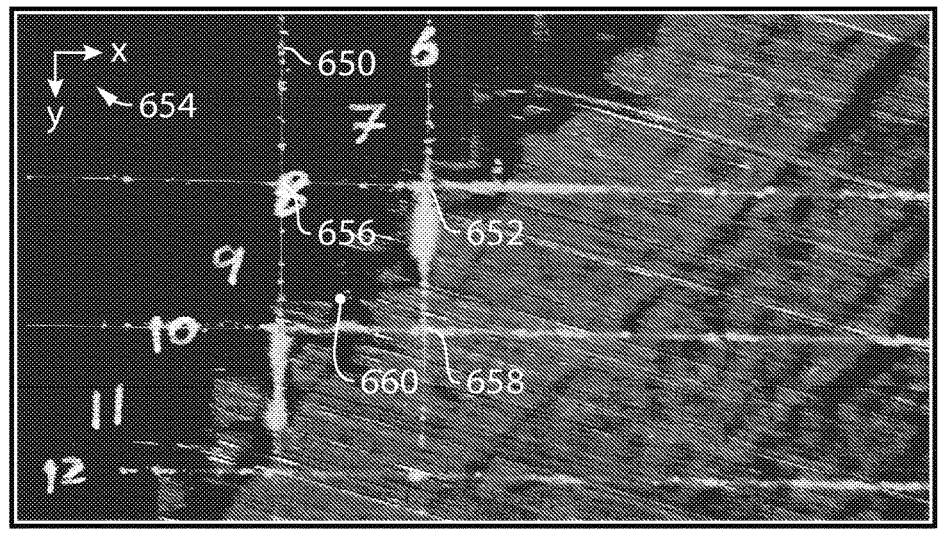
FIG. 7 is an exemplary embodiment of a calibration feature for measuring tow placement.

The calibration features as projected onto the component have at least one point that is known or referenced within the global coordinate system (X, Y, Z). This point may be referred to as the Origin, for illustrative purposes. Acquiring an image of the component with the calibration features projected thereon allows a transformation of the image coordinate system to the local curvilinear coordinate system ($P_1$, $P_2$). This is illustrated in FIG. 7, where a calibration feature comprises a grid 650. Point 652 at an intersection (or node) of the grid 650 is the origin of the grid and known in the local coordinate system and in the global coordinate system. The distance between point 652 and other nodes in the grid, such as point 656, is also known in the local coordinate system. The known distance between the two nodes in the grid 650 and information obtained from the image may be used to correlate a pixel size to a dimensional value in the x-direction and in the y-direction in the local coordinate system.

Figure 8A:
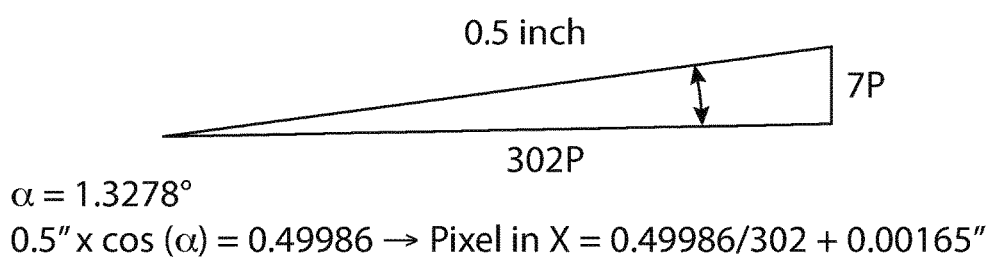
FIGS. 8a and 8b are an exemplary embodiment of converting pixels to dimensional values in x and y directions.
Figure 8B:
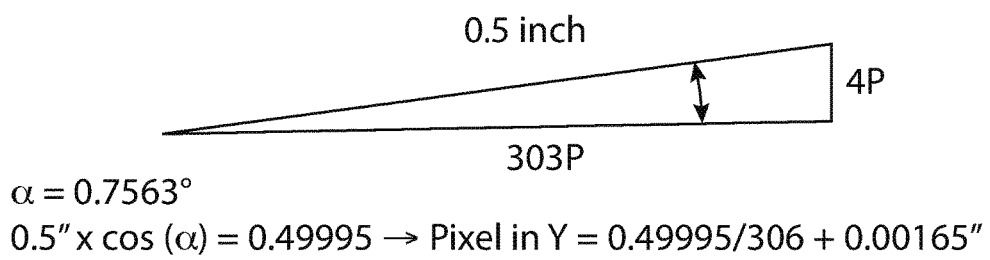

In the image coordinate system 654, point 652 is determined to lie at a given position, for example (862,369). Point 656 is determined to lie at another given position in the image coordinate system 654, for example, at (560, 362). Therefore, from the two points 652, 654, the distance in pixels in the image coordinate system is $\Delta X=302$, $\Delta Y=7$. Similarly, point 658 is determined to lie at, for example, (858, 672). Therefore, from the two points 652, 658, the distance in pixels in the image coordinate system are $\Delta X=4$, $\Delta Y=303$. One exemplary method of determining the dimensional value of a pixel for the two principle directions of x and y is shown in FIGS. 8a and 8b. Assuming a known distance of 0.5 inches between two nodes of the grid 650, the angle α may be determined mathematically using the ΔX and ΔY values previously obtained. The pixel size for each direction may then also be obtained mathematically. In this example, a pixel in X=0.00165 inches, and a pixel in Y=0.00165 inches. Note that the pixel dimension in one direction may differ from the pixel dimension in the other direction. This will depend on the curvature of the component and other dimensional parameters associated with both the component and the calibration feature.

With the pixel dimension in two directions, and the at least one point that is known or referenced within the global coordinate system (X, Y, Z), it becomes possible to obtain inspection/measurement data in order to measure fabrication features such as ply/tow location, angle deviation, and gap size in the local coordinate system and in the global coordinate system. Note that the calibration procedure described above should be repeated for each new location on the component, as the component is three-dimensional and varies in depth. Calibration should also be repeated every time the image acquisition device 602 is displaced along the rails 614 or is zoomed, panned, or tilted.

Tow location may be determined by identifying a point in the image and transforming it to obtain its position in the local coordinate system. For example, If a tow end (identified as point 660 in FIG. 7) is found to be at (693,610) in the image, the distance in pixels from the origin in the image coordinate system is ΔX=169, ΔY=241. Using the previously determined 0.00165 inches as pixel length in the X and Y directions in the local coordinate system, the tow end in the local coordinate system is found as follows:

$$\Delta X = 169 \times 0.00165 = 0.27885''$$

$$\Delta Y = 241 \times 0.00165 = 0.39765''$$

Knowing that the tow is found in the negative X direction from the origin, the position of the point 660 in the local coordinate system is (−0.27885, 0.39765). This position may then be transformed into the global coordinate system using, for example, a CAD model.

Figure 9A:
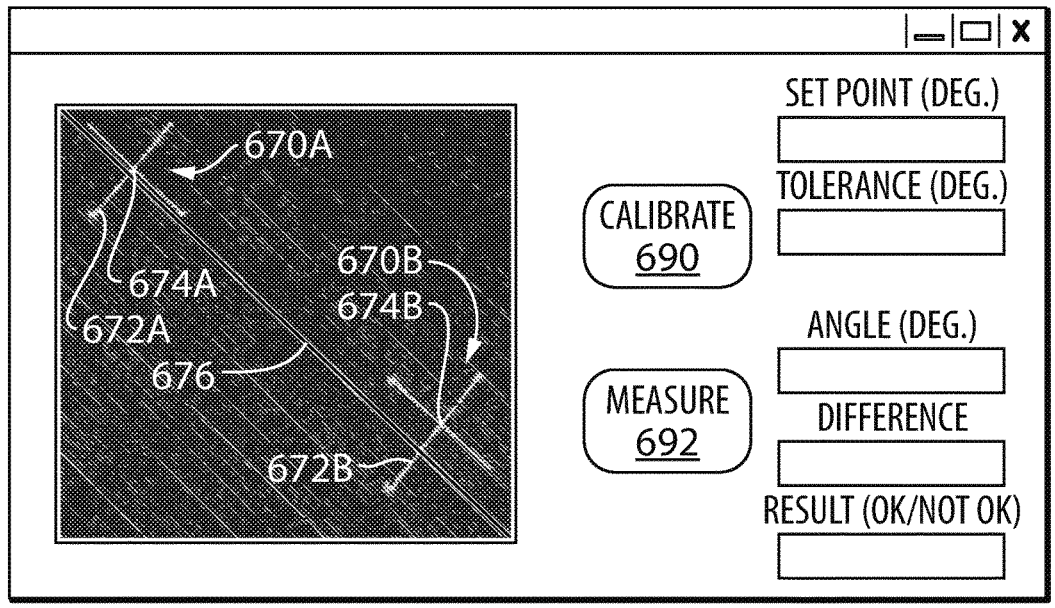
FIG. 9a is an exemplary embodiment of a calibration feature for measuring angle deviation.
Figure 9B:
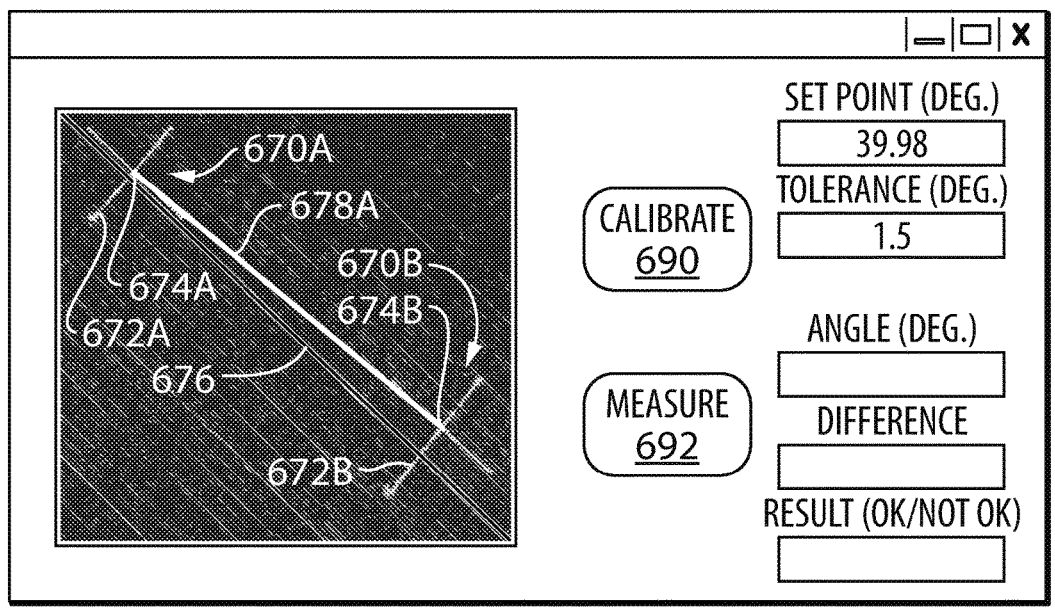
Figure 9C:
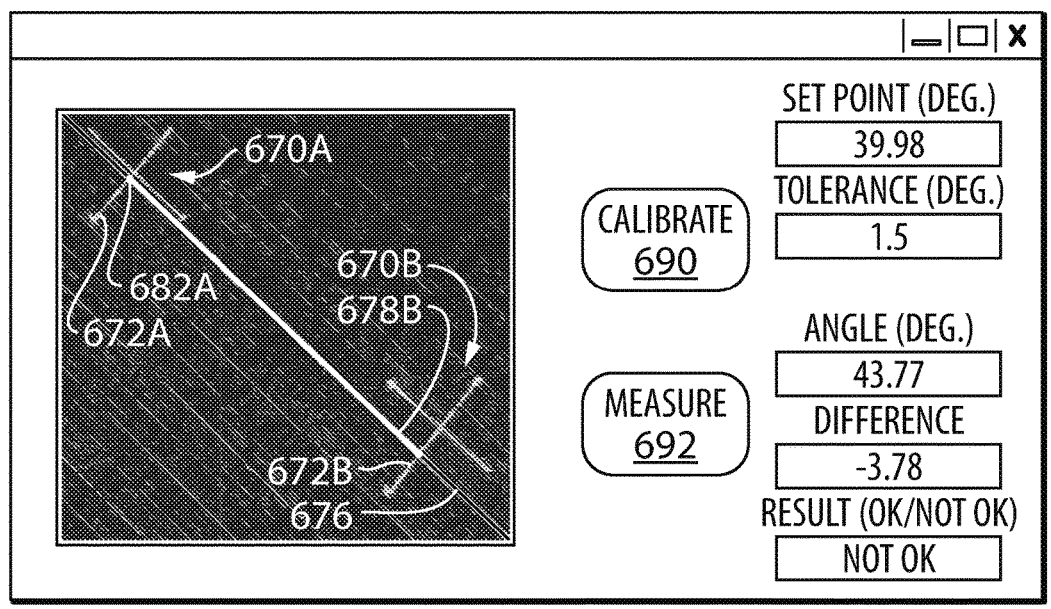

Angle deviation measurements may be obtained using a similar technique to tow location measurements. For example, the coordinates for a first point and a second point may be determined from an image using the same procedure as that used to find point 660 in the image of FIG. 7. The angle between the two points may then be obtained using various calculations, manually or automatically. Alternatively, an angle deviation measurement may be obtained without using dimensional information of pixels, directly from the image. An example of this embodiment is illustrated in FIGS. 9a to 9c. FIG. 9a illustrates an embodiment of a calibration feature for angle deviation measurement. A pair of crosses 670a, 670b are projected onto an image within a field of view showing a fiber 676 for which angle deviation measurement is to be obtained. The crosses 670a, 670b, have respective intersections 674a, 674b and have respective lines 672a, 672b that are positioned to extend over fiber 676. FIG. 9b illustrates a calibration step. By selecting the intersection points 674a, 674b on the image, a line 678a is drawn therebetween. This line 678a acts as the nominal angle, as predetermined by the relative position of cross 670a to cross 670b. Graphical control element 690 may be activated to calibrate the image and output a set point as calibrated. In this example, a tolerance (in degrees) is also output during the calibration step. FIG. 9c illustrates a measurement step. By selecting points 682a, 682b, which represent the points of intersection between lines 672a, 672b and fiber 676, respectively, a line 678b is drawn therebetween. This line 678b acts as the actual angle measurement of the fiber 676. The controller 605 may thus compare the nominal angle with the actual angle upon activation of graphical control element 692 and determine a difference. This difference may be displayed as the angle deviation. It may also be compared to a tolerance for angle deviation and a pass/fail indicator may be presented to the user.

Figure 10:
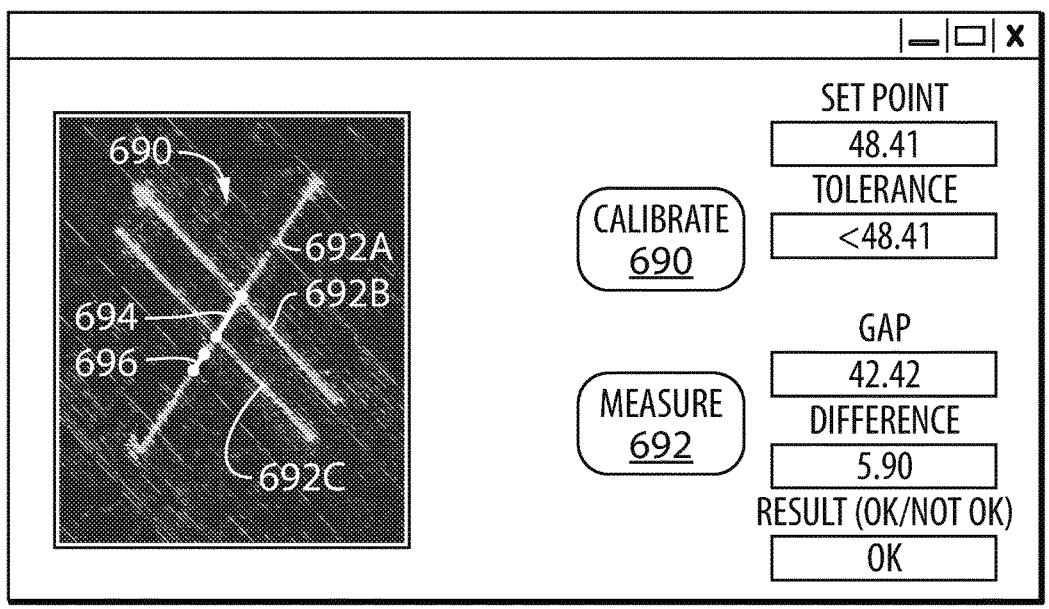
FIG. 10 is an exemplary embodiment of a calibration feature for measuring a gap size.

Gap size measurements may be obtained using a technique similar to tow location measurements. For example, the coordinates for a first point and a second point may be determined from an image using the same procedure as that used to find point 660 in the image of FIG. 7. The distance between the two points may then be obtained using a difference calculation, either manually or automatically. Alternatively, a gap size measurement may be obtained directly from the image without finding the position of two points in the local coordinate system. Instead, a pixel count of a gap may be obtained and converted into a dimensional value using known values of a projected calibration feature. FIG. 10 illustrates an exemplary embodiment of this method. A calibration feature 690 comprising three lines 692a, 692b, 692c forming a double-cross is projected onto the component and its image is acquired. A nominal gap size is built into the calibration feature 690 using the spacing 694 between the intersection points of lines 692b and 692c along line 692a. This distance is known in the global coordinate system. A calibrated value for the set point (or nominal gap size) may be displayed upon activation of graphical control element 690. The measured gap size 696 is found using a pixel count along line 692a upon activation of graphical control element 692. In one embodiment, the pixel count for gap size 696 can be compared to a pixel count for gap size 694 and a difference may be displayed. This difference may be converted into dimensional values using the known size of spacing 694. Alternatively, the pixel counts may themselves be converted into dimensional values using the known size of spacing 694 and the dimensional values may be compared to obtain a difference.

The controller 605 may thus be configured to perform inspection of dimensional tolerances using a pass/fail method with the inspection features. It may also be configured to perform inspection of dimensional tolerances by obtaining actual measurements using the calibration features. In some embodiments, the controller 605 is configured to use both calibration and inspection features. Use may be selective, based on user selection, or it may be combined, such that the output is both a pass/fail indicator and the corresponding measured data.

Figure 11:
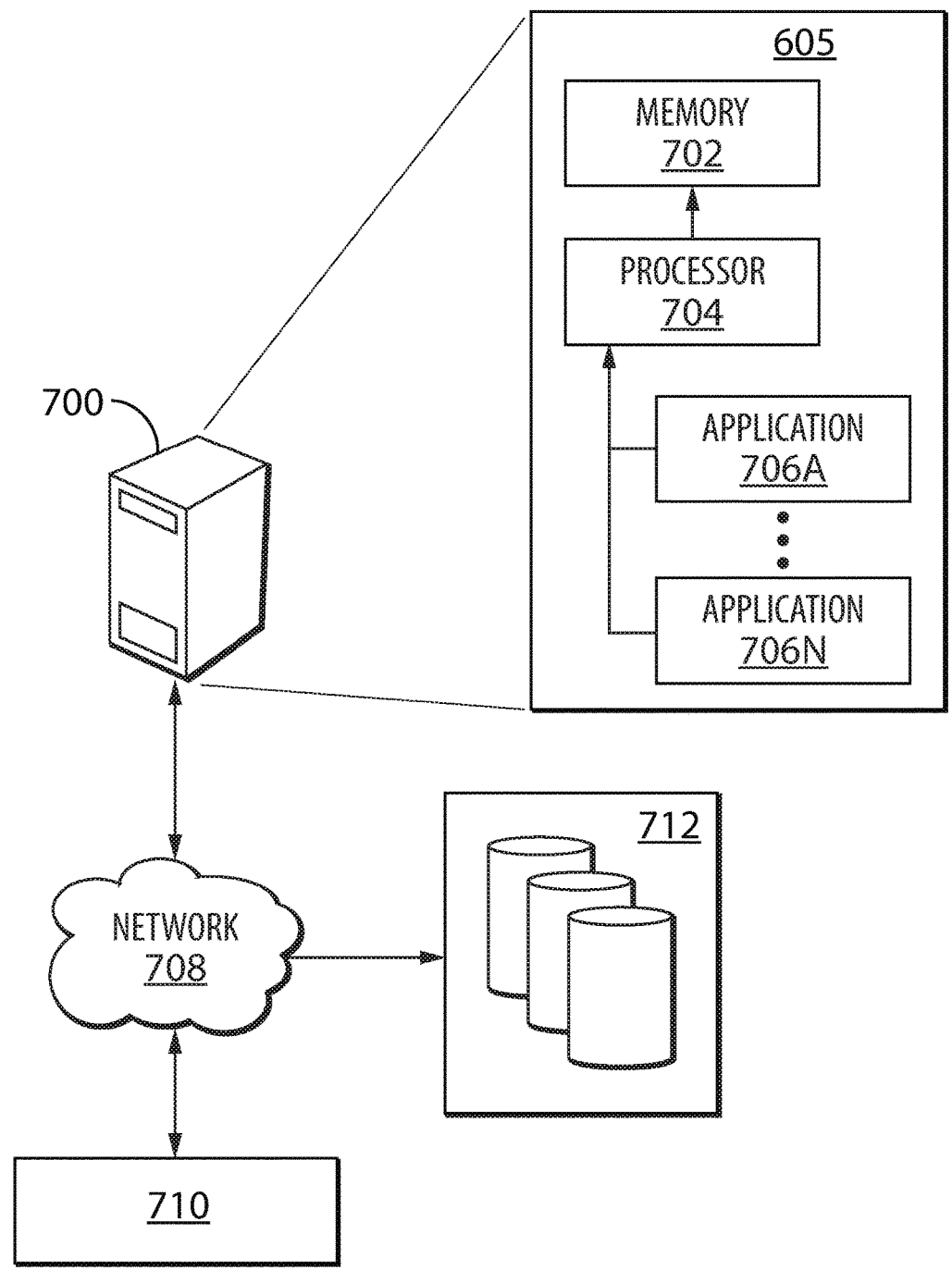
FIG. 11 is an exemplary embodiment for the controller of FIG. 6.

FIG. 11 illustrates an exemplary embodiment for the controller 605. In the embodiment illustrated, the controller 605 is adapted to be accessed by a plurality of devices 710 via a wireless network 708, such as the Internet, a cellular network, Wi-Fi, or others known to those skilled in the art. The devices 710 may comprise any device, such as a laptop computer, a personal digital assistant (PDA), a smartphone, or the like, adapted to communicate over the wireless network 708. Alternatively, the controller 605 may be provided in part or in its entirety directly on devices 710, as a native application or a web application. It should be understood that cloud computing may also be used such that the controller 605 is provided partially or entirely in the cloud. In some embodiments, the application 706a may be downloaded directly onto devices 710 and application 706n communicates with application 706a via the network 708. In some embodiments, the controller 605 may be integrated with the laser projecting device 604 and/or the image acquisition device 602 as a downloaded software application, a firmware application, or a combination thereof.

The controller 605 may reside on one or more server(s) 700. For example, a series of servers corresponding to a web server, an application server, and a database server may be used. These servers are all represented by server 700 in FIG. 11. The controller 605 may comprise, amongst other things, a processor 704 in data communication with a memory 702 and having a plurality of applications 706a, . . . , 706n running thereon. The processor 704 may access the memory 702 to retrieve data. The processor 704 may be any device that can perform operations on data. Examples are a central processing unit (CPU), a microprocessor, and a front-end processor. The applications 706a, . . . , 706n are coupled to the processor 704 and configured to perform various tasks. It should be understood that while the applications 706a, . . . , 706n presented herein are illustrated and described as separate entities, they may be combined or separated in a variety of ways. It should be understood that an operating system (not shown) may be used as an intermediary between the processor 704 and the applications 706a, . . . , 706n.

The memory 702 accessible by the processor 704 may receive and store data, such as a 3D coordinate system, coordinates, fabrication features, inspection features, calibration features, dimensional tolerances, measured data, acquired images, output signals indicative of compliant/non-compliant fabrication features, etc. The memory 702 may be a main memory, such as a high speed Random Access Memory (RAM), or an auxiliary storage unit, such as a hard disk or flash memory. The memory 702 may be any other type of memory, such as a Read-Only Memory (ROM), Erasable Programmable Read-Only Memory (EPROM), or optical storage media such as a videodisc and a compact disc.

One or more databases 712 may be integrated directly into the memory 702 or may be provided separately therefrom and remotely from the server 700 (as illustrated). In the case of a remote access to the databases 712, access may occur via any type of network 708, as indicated above. The databases 712 may also be accessed through an alternative wireless network or through a wired connection. The databases 712 described herein may be provided as collections of data or information organized for rapid search and retrieval by a computer. The databases 712 may be structured to facilitate storage, retrieval, modification, and deletion of data in conjunction with various data-processing operations. The databases 712 may consist of a file or sets of files that can be broken down into records, each of which consists of one or more fields. Database information may be retrieved through queries using keywords and sorting commands, in order to rapidly search, rearrange, group, and select the field. The databases 712 may be any organization of data on a data storage medium, such as one or more servers.

The controller 605 may have one or more applications acting as a control unit, an inspection unit, an image processing unit (IPU), a repair data preparation unit, and a report and archive unit. For example, the control unit may synchronize various subsystems such as a laser projection system, a vision system, and an AFP positioner. The inspection unit may perform tasks such as part identification (for example via barcode reading), saving and processing inspection data, checking for defect density and whether repair is needed, and evaluating operator performance during inspection. The IPU may perform tasks such as replacement of laser patterns with visual patterns, rotation and cropping, line angle calculation, and grid superimposition. The repair data and preparation unit may perform tasks such as obtaining ply location repair data and/or foreign object damage visual inspection repair data, and mapping of defects. The report and archive unit may manage inspection reports, non-conformance reports, and performance reports.

Figure 12A:
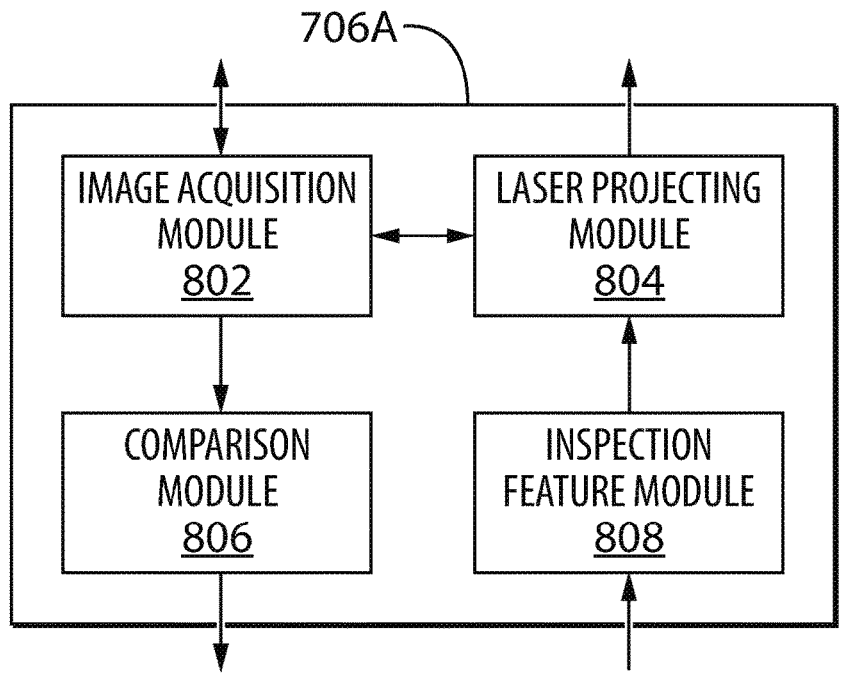
FIGS. 12a, 12b, 12c are exemplary embodiments for applications running on the processor of FIG. 11.

FIG. 12a is an exemplary embodiment for an application 706a running on the processor 704 of the controller 605. The application 706a illustratively comprises an image acquisition module 802, a laser projection module 804, a comparison module 806, and an inspection feature module 808. The inspection feature module 808 may be configured to convert dimensional tolerances into inspection features and provide the inspection features to the laser projecting module 804. As such, it may receive as input dimensional tolerances and coordinates for corresponding fabrication features, either from another application or as entered by a user via an interface. Alternatively, the inspection feature module 808 is configured to receive the inspection features and provide them to the laser projecting module 804. In some embodiments, the inspection feature module 808 may be configured to position the composite component, or the tool on which the composite component sits, in accordance with the coordinates as received for a given fabrication feature.

The laser projecting module 804 may be configured to cause the laser projecting device 604 to scan the targets and to project the inspection features on the composite component. The image acquisition module 802 may be configured to cause the image acquisition device 602 to acquire images of the fabrication features and projected inspection features, and to receive the acquired images. The laser projecting module 804 may be operatively connected to the image acquisition module 802 in order to coordinate projection and image acquisition. As the image acquisition device 602 and/or laser projecting device 604 may be displaceable, positioning thereof may be controlled by the image acquisition module 802 and laser projecting module 804, respectively. The image acquisition module 802 and laser projecting module 804 may also be configured to select from a plurality of image acquisition devices 602 and/or laser projecting devices 604, respectively, as a function of a location of a given fabrication feature on the composite component.

The comparison module 806 may be configured to receive acquired images from the image acquisition module 802. In some embodiments, the comparison module 806 is configured to provide data to a user interface, such as the GUI 502 of FIG. 5, for manual comparison. Alternatively, the comparison module 806 is configured to compare the fabrication feature and the inspection feature to determine compliance of the fabrication feature with the dimensional tolerance automatically. The comparison may comprise determining whether the fabrication feature lies within the projected inspection feature. A fabrication feature (or at least a portion of a fabrication feature) that lies within the projected inspection feature may be determined to be a compliant fabrication feature, and a fabrication feature (or at least a portion of a fabrication feature) that lies at least partially outside the projected inspection feature may be determined to be non-compliant. The comparison may also comprise outputting a non-compliant signal for non-compliant fabrication features.

Figure 12B:
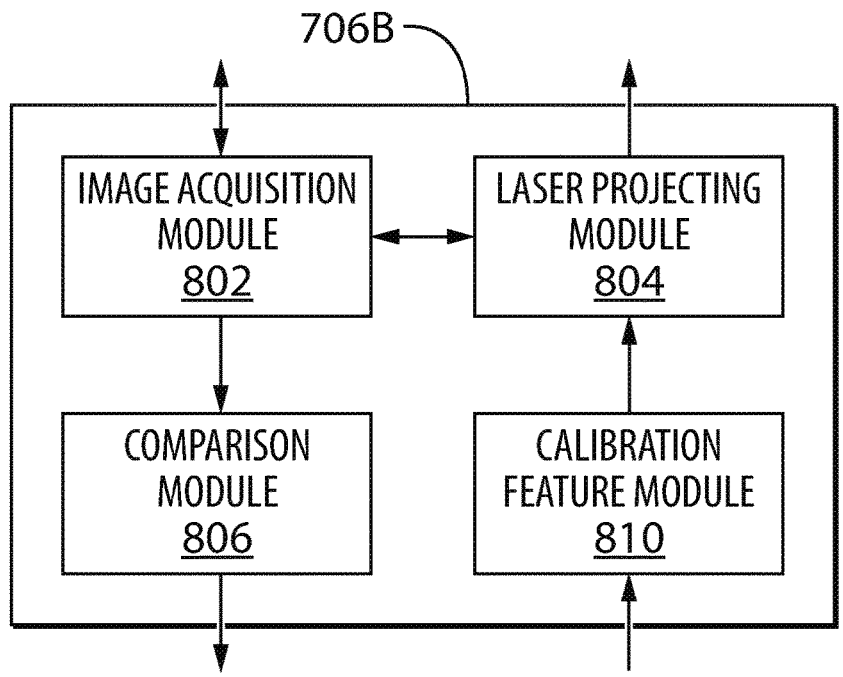

FIG. 12b is an exemplary embodiment for an application 706b running on the processor 704 of the controller 605. The application 706b illustratively comprises an image acquisition module 802, a laser projection module 804, a comparison module 806, and a calibration feature module 810. The calibration feature module 810 may be configured to generate calibration features with nominal values designed therein, such as the double-cross 690 or the pair of crosses 670a, 670b. It may also be configured to generate calibration features with known dimensional data such as a grid or other shape, point, line, etc. As such, the calibration feature module 810 may receive as input dimensional tolerances and coordinates for corresponding fabrication features, either from another application or as entered by a user via an interface. Alternatively, the calibration feature module 810 is configured to receive the calibration features and provide them to the laser projecting module 804. In some embodiments, the calibration feature module 810 may be configured to position the composite component, or the tool on which the composite component sits, in accordance with the coordinates as received for a given fabrication feature. The calibration feature module 810 may be configured to perform a variety of inspection procedures on a component, such as but not limited to male corner measurement, angle deviation measurement, and gap size measurement.

Figure 12C:
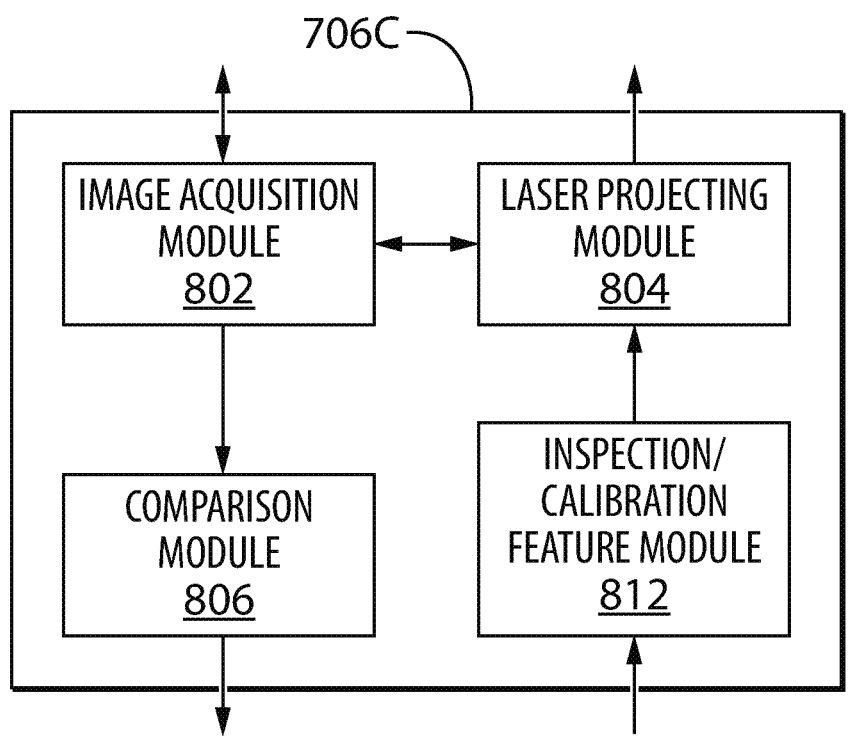

FIG. 12c is an exemplary embodiment for an application 706c running on the processor 704 of the controller 605. The application 706c illustratively comprises an image acquisition module 802, a laser projection module 804, a comparison module 806, and an inspection/calibration feature module 812. The inspection/calibration feature module 812 may be configured to generate inspection/calibration features with nominal values and dimensional tolerances designed therein. As such, the inspection/calibration feature module 812 may receive as input dimensional tolerances and coordinates for corresponding fabrication features, either from another application or as entered by a user via an interface. Alternatively, the inspection/calibration feature module 812 is configured to receive the inspection/calibration features and provide them to the laser projecting module 804. In some embodiments, the inspection/calibration feature module 812 may be configured to position the composite component, or the tool on which the composite component sits, in accordance with the coordinates as received for a given fabrication feature. The inspection/calibration feature module 812 may be configured to perform a variety of inspection procedures on a component, such as but not limited to male corner measurement/inspection, angle deviation measurement/inspection, and gap size measurement/inspection.

The above description is meant to be exemplary only, and one skilled in the relevant arts will recognize that changes may be made to the embodiments described without departing from the scope of the invention disclosed. For example, the blocks and/or operations in the flowcharts and drawings described herein are for purposes of example only. There may be many variations to these blocks and/or operations without departing from the teachings of the present disclosure. For instance, the blocks may be performed in a differing order, or blocks may be added, deleted, or modified. While illustrated in the block diagrams as groups of discrete components communicating with each other via distinct data signal connections, it will be understood by those skilled in the art that the present embodiments are provided by a combination of hardware and software components, with some components being implemented by a given function or operation of a hardware or software system, and many of the data paths illustrated being implemented by data communication within a computer application or operating system. The structure illustrated is thus provided for efficiency of teaching the present embodiment. The present disclosure may be embodied in other specific forms without departing from the subject matter of the claims. Also, one skilled in the relevant arts will appreciate that while the systems, methods and computer readable mediums disclosed and shown herein may comprise a specific number of elements/components, the systems, methods and computer readable mediums may be modified to include additional or fewer of such elements/components. The present disclosure is also intended to cover and embrace all suitable changes in technology. Modifications which fall within the scope of the present invention will be apparent to those skilled in the art, in light of a review of this disclosure, and such modifications are intended to fall within the appended claims.

The invention claimed is:

1. A method for inspecting a composite component, the method comprising:
positioning the composite component in a three-dimensional coordinate system;
causing a laser-generated inspection feature to be projected onto the composite component at a location in the three-dimensional coordinate system corresponding to a fabrication feature of the composite component, the inspection feature having geometric parameters associated with a dimensional tolerance for the fabrication feature;
acquiring an image of the composite component with the inspection feature projected thereon and visible in the image; and
determining compliance of the fabrication feature based on a relative position of the fabrication feature with respect to the inspection feature;
wherein the method is performed as the composite component is manufactured, for each ply of the composite component, and further comprising:
repairing a non-compliant fabrication feature in real-time and causing the inspection feature to be projected onto a ply having a repaired fabrication feature to validate a repair.

2. The method of claim 1, wherein determining compliance of the fabrication feature comprises a visual inspection of the fabrication feature relative to the laser-generated inspection feature.

3. The method of claim 2, further comprising outputting a non-compliant signal for non-compliant fabrication features.

4. The method of claim 1, further comprising converting the dimensional tolerance into the inspection feature.

5. The method of claim 1, wherein the inspection feature is a three-dimensional inspection feature adapted to a shape of the composite component.

6. The method of claim 1, wherein the inspection feature is a tolerance window having a width W corresponding to the dimensional tolerance.

7. The method of claim 1, wherein the inspection feature is a reference point and a reference line having a length L and positioned with respect to the reference point in accordance with the dimensional tolerance.

8. The method of claim 1, wherein the fabrication feature is one of a tow location, a gap size, and a fiber angle deviation.

9. The method of claim 1, wherein the laser-generated inspection feature is projected onto the composite component at a predetermined incident angle with respect to a normal to a surface of the composite component.

10. A system for inspecting a composite component on a manufacturing tool, the system comprising:
at least one laser projecting device configured for projecting an inspection feature onto the composite component at a location corresponding to a fabrication feature of the composite component, the inspection feature having geometric parameters associated with a dimensional tolerance for the fabrication feature; and at least one image acquisition device positioned with respect to the composite component and the laser projecting device to acquire an image of the composite component with the inspection feature projected thereon and visible in the image;

wherein the at least one laser projecting device is configured for projecting the inspection feature for each ply of the composite component as the component is manufactured and for projecting the inspection feature onto a ply having a repaired fabrication feature to validate a repair.

11. The system of claim 10, further comprising a controller operatively connected to at least one of the at least one laser projecting device and the at least one image acquisition device, and configured for controlling at least one of projection of the inspection features and acquisition of images.

12. The system of claim 11, wherein the controller is further configured for converting the dimensional tolerance into the inspection feature.

13. The system of claim 10, further comprising a controller connected to at least one of the at least one laser projecting device and the at least one image acquisition device, and configured for comparing the fabrication feature and the inspection feature to determine compliance of the fabrication feature with the dimensional tolerance.

14. The system of claim 13, wherein the controller is further configured for controlling at least one of projection of the inspection features and acquisition of images.

15. The system of claim 10, wherein the at least one laser projecting device is fixed.

16. The system of claim 10, wherein the at least one image acquisition device is displaceable along a rail or frame.

17. The system of claim 10, wherein the at least one image acquisition device has at least one of panning, tilting and zooming capabilities.

18. The system of claim 10, wherein the at least one image acquisition device is a video camera.

19. The system of claim 10, wherein the at least one laser projecting device is positioned to project at a predetermined incident angle with respect to a normal to a surface of the composite component.

* * * * *